United States Patent [19]

Bombardelli et al.

[11] Patent Number: 4,963,527

[45] Date of Patent: Oct. 16, 1990

[54] **PHOSPHOLIPID COMPLEXES OF EXTRACTS OF *VITIS VINIFERA*, THEIR PREPARATION PROCESS AND PHARMACEUTICAL AND COSMETIC COMPOSITIONS CONTAINING THEM**

[75] Inventors: Ezio Bombardelli, Milan, Italy; Michel Sabadie, Bernay, France

[73] Assignees: INDENA S.p.A., Milan, Italy; SANOFI, Paris, France

[21] Appl. No.: 143,764

[22] Filed: Jan. 14, 1988

[30] Foreign Application Priority Data

Jan. 14, 1987 [IT] Italy ............................ 19084 A/87

[51] Int. Cl.⁵ .................... A61K 31/70; A61K 31/685
[52] U.S. Cl. ........................................ 514/25; 514/78; 536/8; 260/430

[58] Field of Search ................. 514/25, 78; 536/8; 260/403

[56] References Cited

U.S. PATENT DOCUMENTS

| | | | |
|---|---|---|---|
| 4,358,442 | 11/1982 | Wirtz-Peitz et al. | 514/78 |
| 4,764,568 | 8/1988 | Gabetta et al. | 514/78 |

FOREIGN PATENT DOCUMENTS

| | | | |
|---|---|---|---|
| 161445 | 10/1985 | European Pat. Off. | 514/78 |
| 1152632 | 7/1986 | Japan | 514/78 |

*Primary Examiner*—John W. Rollins
*Attorney, Agent, or Firm*—Wegner & Bretschneider

[57] ABSTRACT

Complexes resulting from the reaction of phospholipids, synthetic or of vegetable or animal origin, with flavonoids extracted from *Vitis vinifera*, their use in therapeutics and in cosmetics.

12 Claims, No Drawings

PHOSPHOLIPID COMPLEXES OF EXTRACTS OF VITIS VINIFERA, THEIR PREPARATION PROCESS AND PHARMACEUTICAL AND COSMETIC COMPOSITIONS CONTAINING THEM

The present invention is concerned with complexes of phospholipids and extracts of *Vitis vinifera*, their preparation process and the pharmaceutical and cosmetic compositions containing them.

The extracts of *Vitis vinifera* which can be obtained from the seeds of the plant as described in the patents GB-A-1541469 and FR-A-2092743 are constituted by a mixture of polyphenols, namely in general, (−)epicatechin, the proanthocyanidins $B_1$ and $B_2$, (+)catechin, and their polymerisation derivatives, known under the name of procyanidol (non-proprietary French name) or flavanol oligomers.

The extracts of *Vitis vinifera* are used at present in human therapeutics principally in the treatment of hepatic and vascular diseases or in ophthalmology The mechanism of pharmacological action of these flavonic derivatives, and particularly of the catechic flavonoids, seems bound up principally with their antioxidant activity and their activity as scavengers of free radicals, which is shown by their action on lipid peroxidation processes, their stabilizing effect on membranes and their action on the prostaglandin chain, as well as by their interaction with the humoral and tissue enzymatic systems.

It has now been found that the flavonic derivatives present in the extracts of *Vitis vinifera* form complexes with advantageous properties with natural or synthetic phospholipids, and a first object of the invention is constituted by the complexes formed by the reaction of phospholipids of vegetable, animal or synthetic origin with the extract of *Vitis vinifera*, said phospholipids corresponding to the formula:

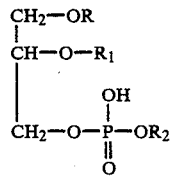

in which R and $R_1$, being identical or different, represent the acyl groups from natural fatty acids such as palmitic, stearic, oleic, linoleic and linolenic acids, while $OR_2$ is derived from an aliphatic amino-alcohol with the formula $R_2OH$, such that $R_2$ represents $CH_2-CH_2-N^+(CH_3)_3$: $CH_2-CH_2-NH_2$: or

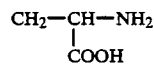

The preferred phospholipids are lecithin from soya or from eggs, phospholipids from brain and skin of cattle or pigs and the phosphatidylcholines, phosphatidylserines and phosphatidylethanolamines, the ester groups of which are derived from the previously mentioned fatty acids.

In the complexes according to the invention, the ratio of the number of molecules of phospholipid to that of flavonoid is in general between 0.5 and 3, and is preferably 1.

The complexes are prepared by the action of the phospholipids on the flavone extracts in an inert solvent: in general, from 1 to 3 parts by weight of phospholipid is made to react with one part of extract; the soluble complexes are isolated by evaporation of the solvent under vacuum, by freeze-drying or after precipitation by addition of a non-solvent to the preparation medium.

The flavonoids in general are insoluble in apolar and aprotic solvents, such as the chlorinated solvents $CHCl_3$ and $CH_2Cl_2$, while the complexes are soluble, because of their lipophilic character; on the other hand, the complexes are decomposed in solvents with a strong dielectric constant, such as dimethylsulphoxide and the alcohols.

The formation of a complex between the molecules of phospholipids and those of the flavonoids has first of all been confirmed by the study of the NMR spectra of the proton, of the carbon 13 and of the phosphorus 31 of complexes of pure products prepared from certain of the flavonoids present in the *Vitis vinifera* extract, and notably with (+)catechin, (−)epicatechin and proanthocyanidine $B_1$, on which phosphatidylcholine from soya or distearoylphosphatidylcholine have been made to react. In the NMR-$^1$H spectrum of the complex, the signals of the protons of the flavonoid molecule are not observed, in contrast to those of the protons of the lipid part, and the broad signal of the protons of the methyls of the $N(CH_3)_3$ group of the choline is enlarged in comparison with the broad signal of the pure product. The relaxation times of the nuclei principally concerned in the formation of the complex are reduced so as to make all the signals of the flavonoid and of the choline and glyceryl groups of the phospholipid disappear on the NMR$^{13}$C spectrum. Finally, the phosphorus signal is enlarged and displaced on the spectrum of the 31P.

The medicaments containing the complexes are a further object of the invention. In effect, the complexes of the invention, like the starting flavanol oligomers, present a vascular protecting activity; in particular, they reduce the capillary permeability and fragility, as is shown by the results obtained in the test of the capillary permeability to histamine in the rat, the methodology of which has been described by K. UDAKA et coll., in: Proc. Soc. Exp. Biol. Med. 133, p.1384 (1970); this activity is greater than that of the starting oligomers.

Furthermore, when they are administered by topical route, the complexes have an anti-oedematous and cicatrizing activity which is not shown by the flavanol oligomers from which they are prepared. This activity is shown by the test of inhibition of oedema to croton oil, the methodology of which is described by Tubaro et coll., in Agents and Actions 17¾ p. 347-349 (1985).

The medicaments of the invention can be used in a form suitable for administration by oral route, such as tablets, capsules or pills, for the treatment of veno-lymphatic insufficiencies such as heavy legs, cramps, pains, paresthesia, oedemas, or for the treatment of disorders of retinal or choroidal circulation; as a general rule, they are adminstered at doses of 5 mg to 250 mg per day, according to the nature and the importance of the disorder to be treated.

The medicaments for topical administration are presented in the form of a cream containing from 0.1 to 10% by weight of active ingredient which can be applied once or several times a day, on the healthy skin for the treatment of heavy legs, cramps and oedemas in particular of the lower members, or on wounds to favour their healing or also in cutaneous eruptions to reduce the oedema.

Cosmetic compositions including complexes of phospholipids and flavonoids of extracts of *Vitis vinifera* are a further object of the invention. The complexes, because of their properties as anti-oxidants, scavengers of free radicals, and protectors of cutaneous lipids, reduce the attacks of aggressive agents on the skin and slow down its aging.

They are advantageously introduced into sun protective compositions, to be used before or after exposure to the sun, in daily protection products such as day-face creams or make-up base, or also in make-up products such as colour bases, creams for cheeks or eyelids and lipsticks and shines for lips.

Furthermore, because of their activity in protecting the cutaneous microcapillaries, they are introduced with advantage into antiacne rosacea products.

Generally, the complexes according to the invention are introduced into cosmetic compositions at 0.01 to 1% by weight.

In what follows, examples are described of putting the invention into operation as well as the preparation of complexes of (+)catechin, (−)epicatechin, and proanthocyanidin B, used in the study of nuclear magnetic resonance.

(a) complex of (+)catechin and distearoylphosphatidylcholine: a suspension of 2.9 g of (+)catechin and 8 g of distearoylphosphatidylcholine in 50 ml of methylene chloride is maintained at the reflux temperature of the solvent until total solution has taken place.

After concentration, the residue is introduced into 150 ml of n-hexane where the complex precipitates. In this way, 10.5 g of white product is obtained, m.p. 159°-160° C., and of which the UV absorption at 280 nm in $CH_3OH$ is $E_{1\%}=39.4$. On the NMR-$^1$H spectrum, the peaks of the aromatic protons between 7 and 5.5 and that of the aliphatic protons between 2.3 and 4.8 and between 3.9 and 4.6 (H on the carbons carrying O) and towards 3.4 (H on the $N(CH_3)_3$) have disappeared.

(b) complex of (−)epicatechin and soy phosphatidylcholine.

A solution of 2.9 g of (−)epicatechin and 7.8 g of 95% soy phosphatidylcholin, sold under the name LIPOID S 100, in 30 ml of dioxan is freeze-dried to yield 10.6 g of a product having a melting point of 170°-172° C., and $E_{1\%}=40.7$ at 280 nm ($CH_3OH$). On the NMR-$^1$H spectrum in $CCl_3$, unresolved signals are observed between 6.7-6.9; 5.1-5.3; 3.8-34.4; 2.6-3.1 ppm and those of the olefinic protons at 5.2 ppm.

(c) complex of proanthocyanidin $B_1$ and soy phosphatidylcholine.

A solution of 5.8 g of proanthocyanidin $B_1$ and 7.8 g of 95% soya phosphatidylcholine in 100 ml of a mixture of methylene chloride and methanol 9/1 (V/V) is taken to dryness and the residue is redissolved in methylene chloride. The solution is then concentrated to 30 ml and poured into 150 ml of n-hexane: the precipitate formed is isolated and dried under vacuum at 60° C.

In this way 13.1 g of a complex is obtained with a melting point of 128°-129° C. and $E_{1\%}=75$ at 280 nm in $CH_3OH$.

On the NMR-$^1$H spectrum in $CDCl_3$, large unresolved bands are observed between 6.7-6.9; 5.1-5.3; as well as the peak of the olefin protons at 5.2 ppm, those of the methylenes between 1.5 and 1.1 and of the methyls at 0.9 ppm.

EXAMPLE 1

Complexes of a purified extract of procyanidol oligomers of *Vitis vinifera* with soya phosphatidylcholine The extract is prepared as described in FR-A-2092743. 10 g of this extract and 15 g of 95% soy phosphatidylcholine are dissolved in 250 ml of methylene chloride containing 5% by volume of methanol. The solvent is evaporated until a pasty residue is obtained which is dissolved in 300 ml of methylene chloride. The solution is then concentrated to 50 ml under ordinary pressure, and poured into 300 ml of n-hexane.

A precipitate appears which is isolated and dried for 24 hours under a vacuum at 60° C. 23 g of a complex is obtained, with melting point 105° C., soluble in non-polar solvents. On the NMR-$^1$H spectrum, a broad band is observed between 6.7 and 7 ppm, the peak of the olefin protons at 5.2 ppm, that of the methylene between 1.5 and 1.1 ppm and that of the methyls at 0.9 ppm.

In table I are shown the results of the test of the capillary permeability to histamine.

TABLE I

| PRODUCT | NUMBER OF ANIMALS | DOSE | % INHIBITION |
|---|---|---|---|
| (control) | 8 | | |
| Procyanidol oligomers | 8 | 50 | −16.81 |
| | 8 | 100 | −22.05 |
| | 8 | 200 | −22.44 |
| Complex | 8 | 50 | −23.51 |
| | 8 | 100 | −26.96 |
| | 8 | 200 | −30.69 |

In table II the results are shown of the test for oedema with croton oil; the products were deposited on the skin.

TABLE II

| PRODUCT | DOSE mg | NUMBER OF ANIMALS | OEDEMA mg | % INHIBITION |
|---|---|---|---|---|
| (control) | — | 8 | 5.3 ± 0.5 | |
| oligomers | 300 | 8 | 4.7 ± 0.9 | 16 |
| complex | 750 | 8 | 2.6 ± 0.4 | 54 |

EXAMPLE 2

Complex of procyanidol oligomers and distearoylphosphatidylcholine 3.2 g of oligomers and 7.9 g of 99% L-alpha-distearoylphosphatidylcholine are introduced into 50 ml of a mixture of methylene chloride and methanol 95/5 (V/V); when these have dissolved, the solution is concentrated and treated as described in example 1. In this way, 10.5 g of complex is obtained, m.p. 128.5° C.

NMR-$^1$H Spectrum, ($CCl_3$):

Disappearance of the peaks between 6.4-7 ppm and of those between 8.7-9.2 ppm: attenuation of the signals of methylenes between 1.5 and 1.1 ppm, and enlargement of the broad signal of the N—$CH_3$ at 3.3 ppm.

EXAMPLE 3

Complexes of an extract of *Vitis vinifera* with a natural mixture of soya phospholipids 10 g of an extract of *Vitis vinifera* enriched with procyanidol oligomers and 20 g of a natural mixture of 97% soy phospholipids containing 30% of phosphatidylcholine, 20% of phosphatidylethanolamine, 6% of phosphatidylinositol and other phospholipids are introduced into 200 ml of dioxan.

The dioxan solution is filtered, then freeze-dried. In this way, 33.5 g of a clear beige powder is obtained, quite soluble in chlorated solvents, and of which the NMR-$^1$H spectrum shows that it is a complex.

EXAMPLE 4

Complex of an extract of *Vitis vinifera* with hydrogenated soya phospholipids 10 g of extract and 15 g of hydrogenated soya lecithin marketed by NATTERMAN under the name Phospholipar-R100-H are introduced into 50 ml of acetone and the whole is taken to reflux.

The solution is then concentrated under vacuum and 150 ml of heptane is introduced on the pasty residue. The precipitate which forms is isolated by filtering. This complex is clear beige in appearance.

EXAMPLE 5

Gastro-resistant tablets of a complex of soya phosphatidylcholine with an extract of *Vitis vinifera*

450 mg tablets were prepared in the usual way with:

| | |
|---|---|
| Complex of example 1 | 250 mg |
| Microcrystalline cellulose | 118 mg |
| Precipitated silica | 3 mg |
| Magnesium stearate | 4 mg |
| Anionic polymer of methacrylic acid and its esters | 12 mg |
| Talc | 8 mg |
| Magnesium carbonate | 8 mg |
| Maize starch | 5 mg |
| Gum arabic | 159 mg |

EXAMPLE 6

Pharmaceutical cream 100 g of cream for topical administration is prepared in the usual way with:

| | |
|---|---|
| Complex from example 1 | 2 g |
| Cetyl alcohol | 15 g |
| Isopropyl myristate | 5 g |
| Carboxylic polymer | 1 g |
| Sodium laurylsarcosinate | 3 g |
| Polysorbate 60 | 3 g |
| p-hydroxybenzoates | 0.2 g |
| Perfume | 0.2 g |
| Demineralized water | balance for 100 g |

EXAMPLE 7

Sun emulsion 100 g of emulsion is prepared in the usual way with:

| | |
|---|---|
| Vegetable oil | 1.0 g |
| Mineral oil | 1.8 g |
| Lanolin alcohols | 0.2 g |
| Bentone gel of propylene glycol caprate and caprylate | 5.0 g |
| Cetyl alcohol | 1.7 g |
| Isopropyl palmitate | 4.0 g |
| UVB filter | 2.0 g |
| UVA filter | 2.0 g |
| Polyoxyethylenated lauryl alcohol | 2.5 g |
| Sorbitan stearate | 2.5 g |
| Polyoxyethylenated sorbitan stearate | 1.0 g |
| Tetrasodium EDTA | 0.1 g |
| Carbopol | 0.35 g |
| Preservatives in butyleneglycol | 5.0 g |
| Perfume | 0.3 g |
| Complex of example 1 | 0.2 g |
| Demineralized water | 70.35 g |

EXAMPLE 8

Sun-protecting gel

| | |
|---|---|
| Ceresin | 3.0 g |
| Rice wax | 3.0 g |
| Vegetable oil | 2.0 g |
| Ethyl-2 hexyl palmitate | 44.7 g |
| Bentone gel of propylene glycol caprate and caprylate | 40.5 g |
| Karite-nut butter | 2.5 g |
| UVA and UVB filters | 2.0 g |
| Complex of example 1 | 0.2 g |
| Colouring | 0.02 g |
| Silica | 2 g |
| Perfume | 0.08 g |

EXAMPLE 9

Protective day face cream

| | |
|---|---|
| Stearine | 1.75 g |
| Propyleneglycol monostearate | 2.7 g |
| Isopropyl lanolate | 3.5 g |
| Bentone gel of propylene glycol caprate and caprylate | 6.0 g |
| Isopropyl palmitate | 6.5 g |
| Silicone oil | 3.0 g |
| Sorbitan stearate | 1.8 g |
| Polyoxyethylenated sorbitan stearate | 1.5 g |
| Cetyl alcohol | 0.6 g |
| UVA and UVB filters | 2.0 g |
| Demineralizied water | 64.55 g |
| Tetrasodium EDTA | 0.1 g |
| Aluminium silicate | 0.8 g |
| Carboxymethylcellulose | 0.15 g |
| Propylene glycol | 4.0 g |
| Preservatives | 0.5 g |
| Complexes of example 1 | 0.2 g |
| Perfume | 0.35 g |

We claim:

1. Complexes resulting from the reaction of flavonoids extracted from *Vitis vinifera* with phospholipids selected from the group consisting of soy lecithin, egg lecithin, phospholipids from bovine and porcine brains and skins, and compounds of the formula:

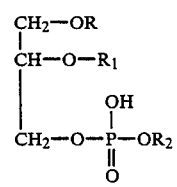

in which R and R$_1$, being indential or different, represent acyl groups from natural fatty acids and R$_2$ represents (CH$_2$)$_2$ N$^+$(CH$_3$)$_3$, (CH$_2$)$_2$NH$_2$, or CH$_2$—CH(COOH)NH$_2$, wherein the molar ratio of phospholipid to flavonoid is between 0.5 and 3.

2. Complexes according to the claim 1, wherein the fatty acids are selected from the group consisting of palmitic, stearic, oleic, linoleic and linolenic acids.

3. Complexes according to claim 1, obtained by reaction of 1 to 3 parts by weight of the phospholipids with 1 part of the *Vitis vinifera* extract.

4. Process for the preparation of the complexes according to claim 1 wherein the phospholipids and the flavonoids are introduced in a solvent having a low dielectric constant and the resulting complexes are recovered after evaporation of the solvent, after their precipitation by addition of a non-solvent, or by freeze-drying.

5. Complexes according to claim 1, wherein the phospholipids are selected from the group consisting of soy lecithin and egg lecithin.

6. Process for the preparation of the complexes according to claim 4 wherein the solvent is selected from $CH_2Cl_2$ or $CHCl_3$.

7. Process for the preparation of the complexes according to claim 4 wherein the solvent further comprises 5% of methanol (V/V).

8. Process for the preparation of the complexes according to claim 4 wherein the solvent is dioxan.

9. Pharmaceutical composition for oral administration comprising from 5 mg to 250 mg of a complex according to claim 1.

10. Pharmaceutical composition for topical administration comprising from 0.1 to 10% by weight of a complex according to claim 1.

11. Cosmetic composition comprising from 0.01 to 1% weight of a complex according to claim 1.

12. A method of protecting skin against the sun comprising applying to the skin an effective amount of the cosmetic composition according to claim 7.

* * * * *